United States Patent
Tashiro et al.

(10) Patent No.: US 8,457,379 B2
(45) Date of Patent: Jun. 4, 2013

(54) METHOD FOR QUANTIFYING ORGAN MOTION, APPARATUS THEREFOR, METHOD FOR ESTIMATING ORGAN POSITION, APPARATUS THEREFOR, METHOD FOR IRRADIATING RADIATION, APPARATUS THEREFOR, AND APPARATUS FOR DETECTING ABNORMAL ORGAN

(75) Inventors: Mutsumi Tashiro, Maebashi (JP); Shinichi Minohara, Chiba (JP)

(73) Assignees: National Institute of Radiological Sciences, Chiba-shi (JP); National University Corporation Gunma University, Maebashi-shi (JP)

( * ) Notice: Subject to any disclaimer, the term of this patent is extended or adjusted under 35 U.S.C. 154(b) by 1162 days.

(21) Appl. No.: 11/920,254

(22) PCT Filed: May 12, 2006

(86) PCT No.: PCT/JP2006/309593
§ 371 (c)(1),
(2), (4) Date: Dec. 11, 2007

(87) PCT Pub. No.: WO2006/121164
PCT Pub. Date: Nov. 16, 2006

(65) Prior Publication Data
US 2009/0022379 A1 Jan. 22, 2009

(30) Foreign Application Priority Data
May 13, 2005 (JP) .................................. 2005-141880

(51) Int. Cl.
*G06K 9/62* (2006.01)

(52) U.S. Cl.
USPC .......................................... 382/131; 382/103

(58) Field of Classification Search
USPC .................................... 382/131, 103
See application file for complete search history.

(56) References Cited

U.S. PATENT DOCUMENTS 7,356,164 B2 * 4/2008 Aliaga et al. .................. 382/103
7,359,535 B2 * 4/2008 Salla et al. ..................... 382/128
(Continued)

FOREIGN PATENT DOCUMENTS

| JP | A-2005-161053 | 6/2005 |
| JP | A-2006-075601 | 3/2006 |
| WO | WO 00/26852 A1 | 5/2000 |

OTHER PUBLICATIONS

Shikata H et al: "An algorithm for localizing branch points of pulmonary vessels for nonrigid registration of the lungs" Systems & Computers in Japan, Wiley, Hoboken, N J, US, vol. 135, No. 3, Mar. 1, 2004, pp. 24-36, XP00253141 7 ISSN: 0882-1 666.*

(Continued)

*Primary Examiner* — Michael Logie
(74) *Attorney, Agent, or Firm* — Oliff & Berridge, PLC

(57) ABSTRACT

A plurality of CT images of an organ (10) which has undergone a subtle variation or deformation are used as input data, blood vessels and trachea 12 distributed inside the organ are extracted and subjected to thinning, the thus thinned images 14 are used to extract the coordinates of bifurcations 16 and connections, the thus extracted coordinates are used as feature points to track the motion of individual points between a plurality of CT images in a three dimensional space, thereby measuring the movement of the organ (10). Thus, it is possible to realize a local motion tracking at an arbitrary point over an entire region inside an organ, which would be impossible by using a metal marker.

15 Claims, 12 Drawing Sheets

U.S. PATENT DOCUMENTS

| | | | | |
|---|---|---|---|---|
| 7,576,741 | B2* | 8/2009 | Matsumoto | 345/424 |
| 7,894,646 | B2* | 2/2011 | Shirahata et al. | 382/128 |
| 2005/0259891 | A1* | 11/2005 | Sendai | 382/294 |
| 2008/0019568 | A1* | 1/2008 | Nishiura | 382/103 |

OTHER PUBLICATIONS

S. Joshi and M. I. Miller, "Landmark matching via large deformation diffeomorphisms," IEEE Trans. Image Process. 1357-1370 (1997).*

Mar. 24, 2010 Supplementary European Search Report issued in European Application No. EP 06 73 2574.

Keall et al., "Four-dimensional radiotherapy planning for DMLC-based respiratory motion tracking", *Medical Physics*, vol. 32, No. 4, pp. 942-951, American Association of Physicists in Medicine, Mar. 16, 2005.

Sohn et al., "110: Automatic deformable registration of the lung for 4D respiratory correlated CT (RCCT) datasets", *Radiology and Oncology*, vol. 76, p. S59, Sep. 1, 2005.

Maintz et al., "A Survey of Medical Image Registration", *Medical Image Analysis*, vol. 2, No. 1, pp. 1-37, Oxford University Press: Oxford, Great Britain, 1998.

Aggarwal et al., "Articulated and Elastic Non-rigid Motion: A Review", *Proceedings of the 1994 IEEE Computer Society Workshop*, Austin, TX, pp. 2-14, IEEE Computer Society: Los Alamitos, CA, Nov. 11, 1994.

Keall, "4-Dimensional Computed Tomography Imaging and Treatment Planning", *Seminars in Radiation Oncology*, vol. 14, No. 1, pp. 81-90, Elsevier Inc., Jan. 2004.

Coselmon et al., "Mutual information based CT registration of the lung at exhale and inhale breathing states using thin-plate splines", *Medical Physics*, vol. 31, No. 11, pp. 2942-2948, American Association of Physicists in Medicine, Oct. 19, 2004.

T. Boskamp et al., "New Vessel Analysis Tool for Morphometric Quantification and Visualization of Vessels in CT and MR Imaging Data Sets", Radiographics, vol. 24, No. 1 (2004) pp. 287-297.

Barnard et al. "Diparity Analysis of Image;" IEEE Transaction of Pattern Analysis and Machine Intelligence; vol. PAMI-2; No. 4; pp. 333-340; Jul. 1980.

Zhang et al; "Technical note: A Novel boundary condition using contact elements for finite element based deformable image.registration;" Med. Phys.; vol. 31; No. 9; pp. 2412-2415; Sep. 2004.

Sarrut et al; "Nonrigid Registration Method to Assess Reproducibility of Breath-Holding with ABC in Lung Cancer;" Int. J. Radiation Oncology Biol. Phys.; vol. 61; No. 2; pp. 594-607; 2005.

Shikata et al; "An algorithim for localizing branchpoints of pulmonary vessels for non-rigid registration of the lung;" The Institute of Electronics Information and Communication Engineers D-II; vol. J84-D-II; No. 7; pp. 1-11; Jul. 2001.

Pisupati C. et al, "Tracking 3-D pulmonary tree structures", Proceedings of the Workshop on Mathematical Methods in Biomedical Image Analysis 21-22, Jun. 1996 San Francisco, CA, USA, Jun. 21, 1996, pp. 160-169, XP009162803.

Sep. 21, 2012 European Office Action issued in European Patent Application No. 06 732 574.6.

* cited by examiner (A)

(B)

METHOD FOR QUANTIFYING ORGAN MOTION, APPARATUS THEREFOR, METHOD FOR ESTIMATING ORGAN POSITION, APPARATUS THEREFOR, METHOD FOR IRRADIATING RADIATION, APPARATUS THEREFOR, AND APPARATUS FOR DETECTING ABNORMAL ORGAN

TECHNICAL FIELD

The present invention relates to a method for quantifying organ motion for quantifying the motion at each voxel position with reference to a three-dimensional digital image at each time point obtained at certain intervals by using high-speed three-dimensional computed tomography (CT) (so-called four-dimensional CT) for the purpose of ascertaining the matching (registration) of each portion inside an organ with respect to an organ such as a lung which undergoes variation or deformation in association with respiration or the like, the deformation and position of volume of interest of tumors or the like in correlation with a phase of respiratory waveform in radiological diagnosis, treatment planning and medical treatment, an apparatus therefor, a method for estimating an organ position by using the above-described method, an apparatus therefor, a method for irradiating radiation, an apparatus therefor and an apparatus for detecting an abnormal organ.

BACKGROUND ART

A position of a tumor which is to be irradiated on radiation therapy will move by respiration and daily variation or deformation of an organ. In general, X-ray transmission images (two-dimensional images) are used to conduct registration so that an organ to be irradiated (a target) can be placed at a predetermined position on radiation therapy.

For example, regarding an organ which moves in association with respiration, a respiratory gating method is used to give irradiation only to a region where a respiratory waveform is found, thereby reducing redundant irradiation occurring by respiratory motion.

However, this respiratory waveform represents a one-dimensional position at a certain point established on the body surface, and an organ also moves three-dimensionally during irradiation. Therefore, a more accurate irradiation is required to ascertain the motion of the organ at individual positions (the speed and direction of movement), the analysis of which is, however, difficult by referring to two-dimensional images.

In particular, where a lung at which a tumor and normal tissues are greatly different in density is subjected to particle beam therapy, the variation of the organ not only in a direction perpendicular to the irradiation beam (herein after simply referred to as beam) but also in an axial direction of the beam greatly influences a range of the beam, thus, resulting in a fear that the tumor may be irradiated to an excessively small extent or normal tissues may be irradiated to an excessively great extent. Therefore, a technology to three-dimensionally ascertain the motion of an organ is now demanded. However, such a technology has not been established with current clinical practices.

In recent years, several reports have been submitted about research of quantification of positions of an organ three-dimensionally. Most of the reports are those in which a reference point which is a marker for tracking movement is given on the surface of a target organ extracted by using X-ray CT images, and the deformation is calculated by referring to the organ as an elastic body model so that reference points on two CT images can coincide with each other.

However, in this instance, it is necessary to set a feature point artificially. Matching of each position inside an organ does not necessarily reflect actual movement. Furthermore, in order to track a specific movement, a metal marker is used in general. The metal marker is, however, implanted into the body of a patient, thus giving a greater burden to the patient. The marker is also restricted in the position and number, thereby making it difficult to ascertain the motion of an organ in detail.

T. Zhang et. al., "Technical note: A novel boundary condition using contact elements for finite element based deformable image registration," Medical Physics 31 (2004) 2412-2415 (hereinafter referred to as Non-patent document 1) has described that a finite element method is used to calculate a three-dimensional deformation of a lung.

Furthermore, D. Sarrut et. al., "Non-rigid registration method to assess reproducibility of breath-holding with ABC in lung cancer," International Journal of Radiation Oncology, Biology, Physics, 61 (2005) 594-607 (herein after referred to as Non-patent document 2) has described that gradients of voxel values obtained by three-dimensional CT images of the lung are compared to quantify the deformation inside the organ and also discussed the deformation of volume of interest at a tumor portion.

Still furthermore, Hidenori Shitaka, et. al., "An algorithm for localizing branchpoints of pulmonary vessels for non-rigid registration of the lung" The Institute of Electronics Information and Communication Engineers D-II, Vol. J84-D-II, No. 07 pp. 1-11 (herein after, referred to as Non-patent Document 3) has described the tracking of movements at vessel bifurcations for matching inside the organ with the deformation of a lung in association with respiratory motion.

However, the technology described in Non-patent Document 1 has a problem that the outer configuration of an organ does not necessarily coincide with the deformation inside the organ.

Furthermore, the technology described in Non-patent Document 2 does not track an anatomical feature inside an organ, thereby posing a problem regarding the accuracy of volume-of-interest deformation.

Still furthermore, the technology described in Non-patent Document 3 is only to position vessel bifurcations.

DISCLOSURE OF THE INVENTION

The present invention has been made for solving the above problems, an object of which is to accurately quantify the motion of an organ.

The present invention has solved the above-described problems by procedures in which a plurality of CT images of an organ which has undergone a subtle variation or deformation are used as input data, blood vessels and trachea distributed inside the organ are extracted and subjected to thinning, the thus thinned images are used to extract coordinates of bifurcations and connections, the thus extracted coordinates are used as feature points to track the motion of individual points between a plurality of CT images in a three dimensional space, thereby measuring movement of the organ.

Furthermore, the feature points are tracked by conducting point pattern matching in which a plurality of CT images and feature point coordinates are used.

Still furthermore, a plurality of the feature points are interpolated for movement, thereby ascertaining movement at an arbitrary point.

In addition, the present invention is to provide a method for estimating an organ position in which dynamic information obtained by the above method is correlated with information on cyclic movements of an organ, thereby estimating the position of the organ.

Furthermore, the information on cyclic movements of the organ is processed into a pneumogram.

The present invention is also to provide a method for irradiating radiation in which radiation is irradiated to a position of the organ estimated by the above-described method.

Still furthermore, the radiation is made changeable in timing and/or position of irradiation.

The present invention is also to provide a method for irradiating radiation in which dynamic information obtained by the above-described method is collected at the same time with a pneumogram, and the correlation between the pneumogram and three-dimensional movements at a target position is ascertained, thereby making it possible to optimize the timing of respiratory gating irradiation on radiation therapy and estimate the target border position for target tracking irradiation at a high accuracy.

Furthermore, the present invention is to solve the previously described problems by using an apparatus for quantifying organ motion which is provided with means for obtaining a plurality of CT images of an organ which has undergone a subtle variation or deformation, means for extracting and thinning blood vessels and trachea distributed inside the organ, means for extracting the coordinates of bifurcations and connections by using the thus thinned images, and means for measuring movement of the organ by using these coordinates as feature points to track the motion of individual points between a plurality of CT images in a three dimensional space.

Still furthermore, the apparatus for quantifying organ motion is provided with means for tracking the feature points by conducting point pattern matching in which a plurality of CT images and feature point coordinates are used.

The apparatus for quantifying organ motion is also provided with means for interpolating movement of a plurality of feature points, thereby determining movement at an arbitrary point.

The present invention is to provide an apparatus for estimating an organ position which is provided with the above-described apparatus and means for estimating the organ position by correlating dynamic information obtained by the apparatus concerned with information on cyclic movements of an organ.

The present invention is also to provide an apparatus for irradiating radiation which is provided with means for irradiating radiation at an organ position estimated by the above-described apparatus.

The present invention is also to provide an apparatus for irradiating radiation which is provided with the above-described apparatus, means for collecting dynamic information obtained by the apparatus concerned and a pneumogram at the same time and means for ascertaining the correlation between the pneumogram and three-dimensional movements at a target site, thereby making it possible to optimize the timing of respiratory gating irradiation on radiation therapy and estimate the target border position for target tracking irradiation at a high accuracy.

The present invention is also to provide an apparatus for detecting an abnormal organ which is provided with the above-described apparatus and means for ascertaining a locally abnormal deformation of an organ on the basis of dynamic information obtained by the apparatus concerned.

In the present invention, attention is given to the anatomical feature of connection, bronchus and/or connection of blood vessels in a lung, for example, and such a fact is utilized that their topology (bifurcations and connections) are retained even if the organ is moved or deformed, thereby measuring the motion of the organ quantitatively. In other words, since the topology of a target is retained before and after the motion, the feature point coordinates are extracted to track the motion of individual points in a three dimensional space, thereby making it possible to measure movement (direction and speed) of the organ which is highly accurate at a local site.

For example, such a fact is utilized that CT values of blood vessels existing along the bronchial tubes are greater than those at the lung region, thereby extracting blood vessels and trachea 12 from CT images, as illustrated in FIG. 1(A).

Then, a thinning algorithm is used to convert the thus extracted blood vessels and tracheal parts to a thinning image 14 which is one voxel in thickness, thereby identifying coordinates of feature points (bifurcations 16 in FIG. 1) of blood vessels or the trachea, which is used as feature points of motion tracking. Thereby, it is possible to provide a local motion tracking at an arbitrary point over an entire region inside the lung, which would be impossible by using a conventional metal marker for tracking movement.

Then, in order to track the displacement of these feature points with respect to two CT images obtained at certain intervals, the two CT images and feature point coordinates are used to conduct point pattern matching. For example, a probabilistic relaxation method is used to conduct the point pattern matching, thereby making it possible to determine a displacement quantity (direction and length) at each feature point so that the displacement of a feature point is consistent with the displacement of a feature point in the neighborhood thereof. In other words, movement can be ascertained at each point by tracking the thus extracted feature points, as illustrated in FIG. 1(B).

Furthermore, interpolation is conducted from these points in a three dimensional space to ascertain movement at an arbitrary point. Therefore, it is possible to determine the displacement quantity with respect to all voxels inside an organ (the lung 10 in the drawing).

The above-described operation is sequentially conducted in CT images obtained continuously, thereby enabling a continuous quantification of motions. Therefore, it is possible to make a four-dimensional dose calculation with respect to a moving target and also give radiation therapy to an organ exhibiting respiratory motion at a higher accuracy.

In the treatment planning of radiation therapy (operation for determining an irradiation method such as direction and frequency of irradiating radiation based on dose calculation and assessment), a tumor portion is set as volume of interest, and irradiating dose calculation is made for the volume of interest and normal tissues around the volume. This operation is conventionally given to static three-dimensional CT images. In contrast thereto, according to the present invention, CT images obtained by using a four-dimensional CT can be used to conduct the operation in a dynamic target. Thus, the deformation of the volume of interest can be automatically calculated to eliminate the necessity for setting the volume of interest to the CT images obtained at each time point. Thereby, it is possible to make more realistic a four-dimensional treatment planning.

Furthermore, three-dimensional digital images obtained sequentially in chronological order from a four dimensional CT which has been developed recently and finding wide application across clinical practices are used to conduct sequential operations of the present invention, thereby making it possible to obtain three-dimensional movements of an organ over a certain time range.

Therefore, dynamic information obtained by the present invention is correlated with reference information such as respiratory waveform, thereby making it possible to estimate movement (three-dimensional direction and the speed therefor) of an organ at an arbitrary time point.

Furthermore, the present invention is made up of a method for obtaining feature points of movement and a method for tracking movement of the feature points, by which it is possible to find an application at various sites by modifying a method for obtaining the feature points as with a case where, for example, angiography is used to obtain X-ray CT images of the liver.

As described above, an organ is ascertained for three-dimensional movement, thereby making it possible to reduce to a greater extent an irradiation margin which must be established conventionally due to a positional uncertainty, inhibiting an unnecessary exposure of normal tissues to radiation and also decreasing radiation damage such as late effect.

An anatomically degenerated organ will cause a distorted movement or a locally abnormal deformation of an organ. However, the present invention can be used in medical diagnosis by making a quantitative comparison with motions during normal time or at normal sites to detect the distortion or abnormality of local movements. For example, the present invention is able to provide a clue to the existence of a tumor and symptoms of pulmonary fibrosis, radiation damage to normal tissues of the lung, which is difficult to distinguish by referring to CT values.

BEST MODE FOR CARRYING OUT THE INVENTION

Hereinafter, a detailed explanation will be made for embodiments of the present invention by referring to drawings.

Figure 1:
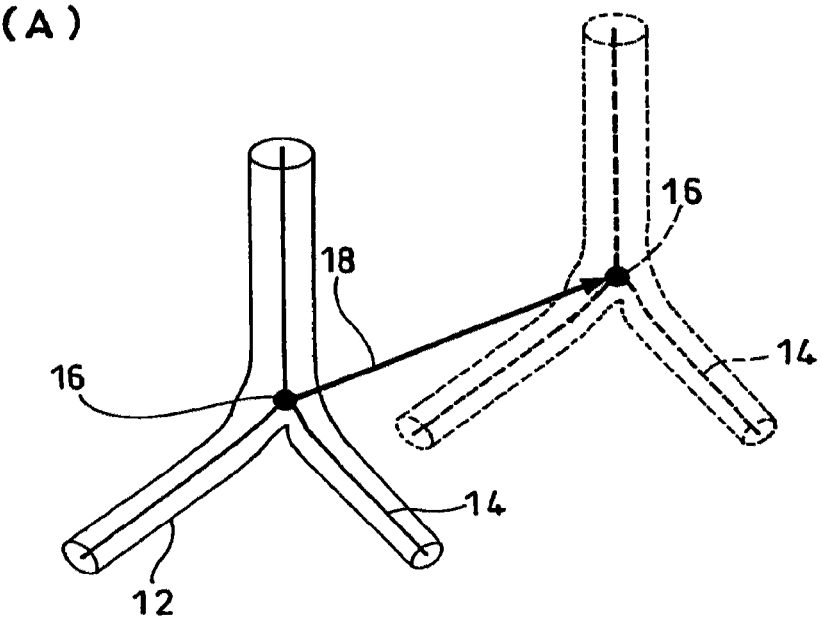
FIG. 1 is a schematic diagram illustrating the quantification of motions in the present invention.
Figure 1:
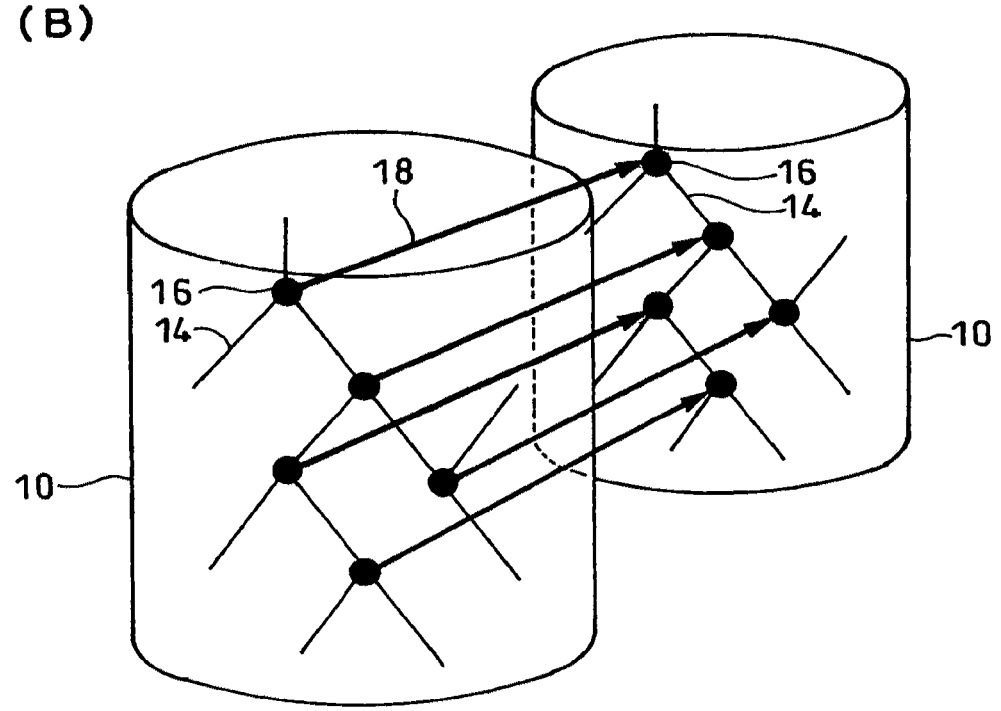
Figure 2:
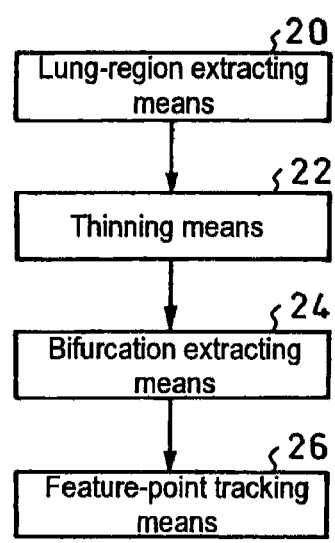
FIG. 2 is a block diagram illustrating a basic constitution of an apparatus for executing a first embodiment of the present invention.

An apparatus for executing the first embodiment of the present invention is that which is constituted as illustrated in FIG. 2 by using, for example, a computer, including lung-region extracting means 20, thinning means 22, bifurcation extracting means 24 and feature-point tracking means 26.

In the thinning means 22, thresholding is conducted by referring to a certain CT value as a threshold value, and the thus obtained figure having one voxel value is cut. However, if parts such as flesh and bones around a lung are left as a result of the thresholding, these parts are also subjected to the thinning process, and they are substantially greater in volume (voxel number) than the bronchial tubes and blood vessels in the lung, thus resulting in greatly extending the calculation time.

Therefore, in order to shorten the calculation time and calculate only a necessary lung region, the lung region is first extracted by using the lung-region extracting means 20.

Figure 3:
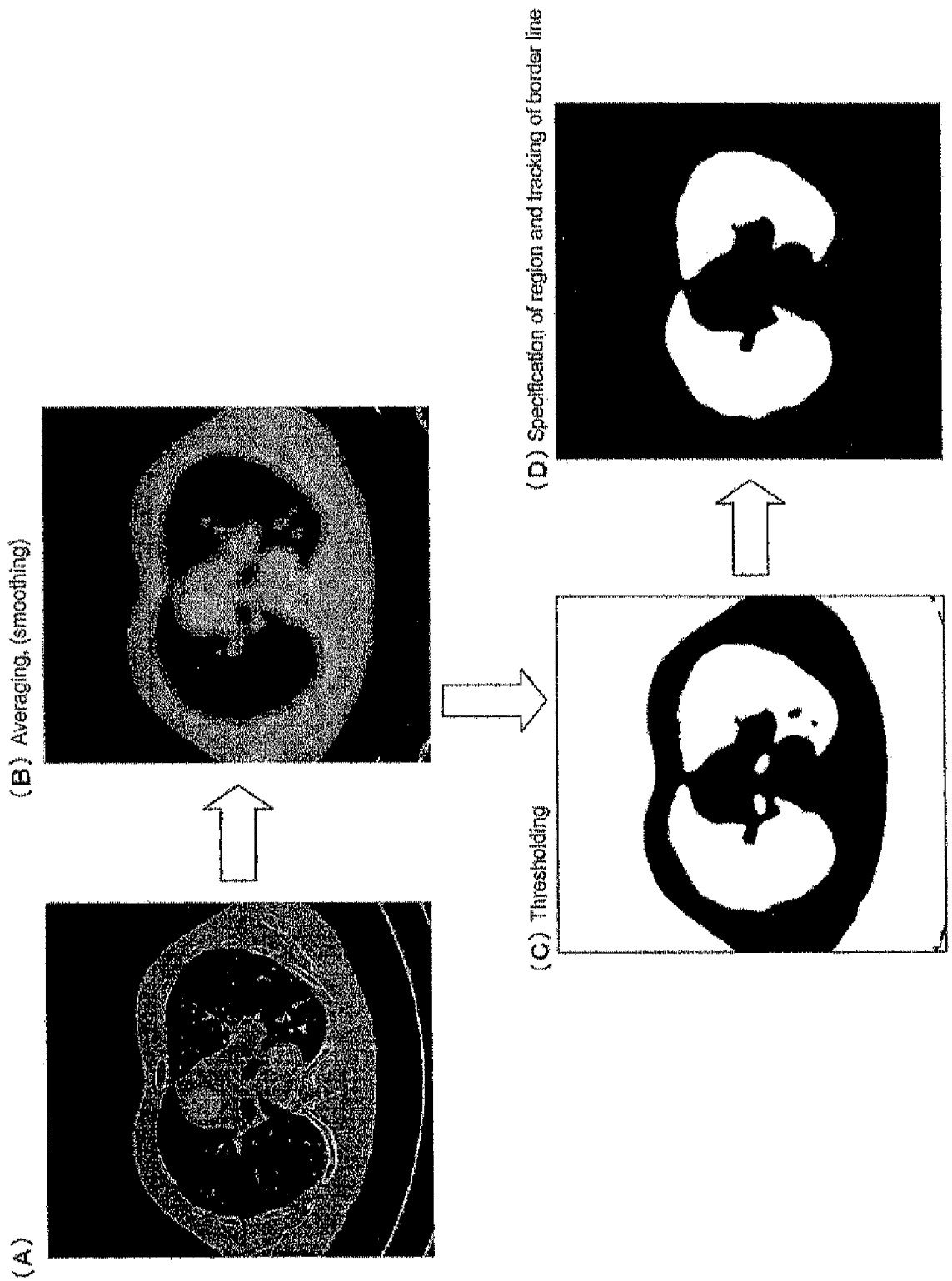
FIG. 3 is a view illustrating procedures for extracting a lung region in the first embodiment.

Specifically, the lung region can be extracted by a method given in FIG. 3. Processing is given to each of two-dimensional CT slice images shown in FIG. 3(A).

First, a smoothing process is conducted for a certain slice image at an established rectangular region, by which the process is conducted at all two-dimensional regions. As illustrated in FIG. 3(B), this process is able to divide the region into a region small in average CT value inside the lung and that high in CT value around the lung. Then, as illustrated in FIG. 3(C), this image is subjected to thresholding on the basis of an appropriate threshold value, thereby extracting only a region small in CT values. Thereafter, the right and left lung regions are specified, by which unnecessary regions such as an external part are removed to extract only a lung region, as illustrated in FIG. 3(D). Operations so far explained are conducted for all the slices, thereby obtaining three-dimensional images of the lung regions. Only the regions obtained herein are to be subjected to the thinning process at a later stage.

Figure 4:
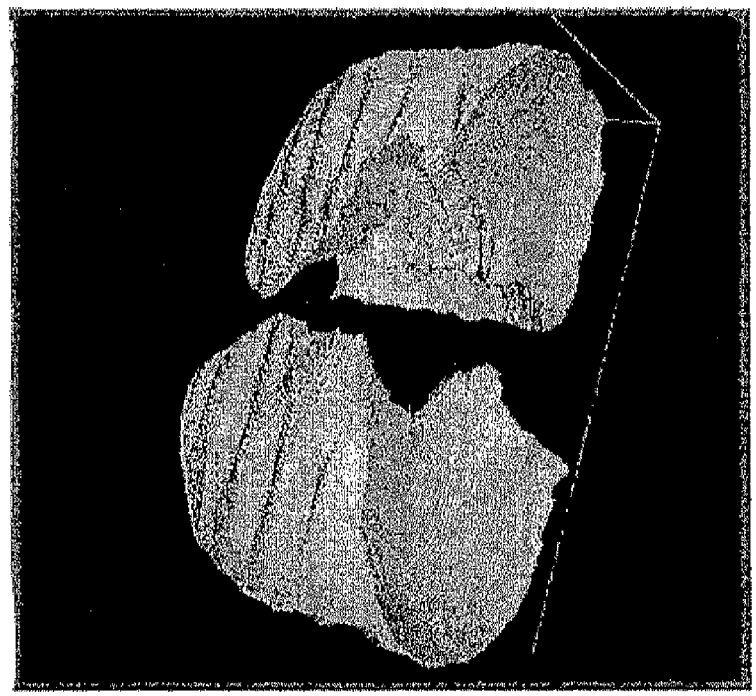
FIG. 4 is a view illustrating the result of extraction in the first embodiment.
Figure 4:
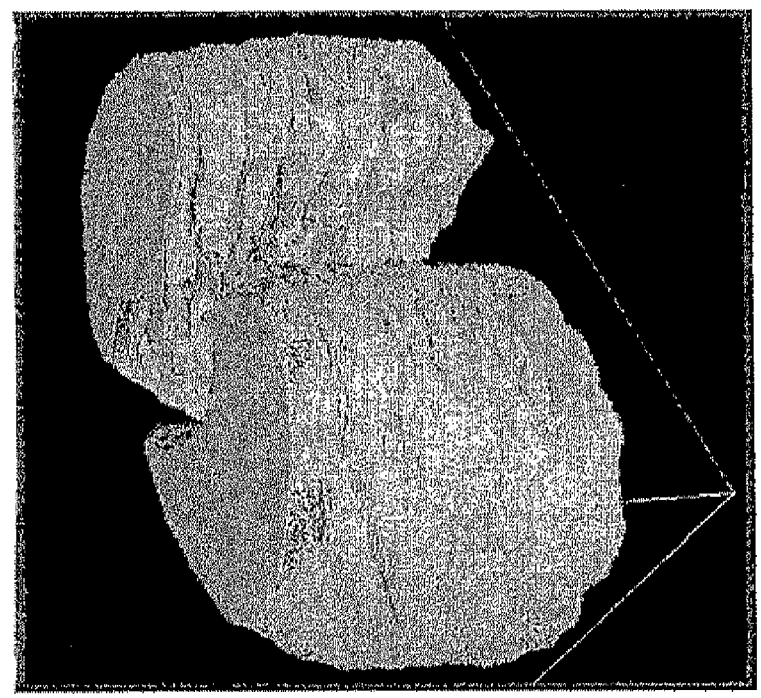

FIG. 4 shows an example of extraction results of the lung regions. Here, an averaged rectangular region size is given to be 15 and a CT threshold value is given to be −500.

The thinning means 22 is to conduct an operation (thinning) in which a figure having the thickness and size is not changed in topology but changed into a line figure matching with a center line of the size 1. This thinning operation makes it possible to specify the coordinates of bifurcations at blood vessels (bronchial tubes) inside the lung in terms of voxel unit. The thus obtained bifurcations are tracked as a feature point of movement, by which movement of the lung can be quantified. A fact that the topology is not changed means that there is no change in characteristics of a figure such as the number of continuous figures and the number of holes or cavities of the figures. Here, a thinning method is used by referring to a sequential algorithm associated with Euclidean distance transformation.

Specifically, first, (1) a three-dimensional CT image is subjected to thresholding by referring to an appropriate CT value as a threshold value. Here, a voxel greater than the threshold value is given as one voxel to be used as a target figure of thinning, whereas a voxel lower than the threshold value is given as zero voxel (background).

Next, (2) images of the lung region extracted by the lung-region extracting means 20 are masked to delete an unnecessary region (a voxel value is given as zero).

Thereafter, (3) an entire image is subjected to the Euclidean square distance transformation process. Thereby, all voxels on a figure receive a maximum square distance from the respective voxels to the background. In this instance, the square distance is used because integer arithmetic is performed and subsequent processes are sufficient only in ascertaining whether the distance is greater.

Next, (4) a deletion judgment is made from voxels smaller in distance. This deletion judgment is able to delete those in which the topology is not changed. First, voxels having a minimum distance value (the outermost value) are checked for whether they can be deleted. Then, undeletable voxels are given as voxels which are stored temporarily. Temporary storage is carried out because it can not be deleted at the present time point in view of retaining topology. However, temporarily stored voxels may be deletable as the deletion process proceeds. The deletable voxels are subjected to permanent storage (established as one voxel) in the case of an endpoint (the number of positive-number voxel of adjacent 26-neighborhood is 1). Other deletable voxels are divided into groups for every three voxels according to the number of positive-number voxels of the adjacent 26-neighborhoods. A deletion judgment is made from image voxels smaller in the number of positive-number voxels (in other words, a part which is isolated and projected to a greater extent). Thereby, it is possible to prevent the occurrence of unnecessary branches resulting from meaningless irregularities on the border surface.

Then, (5) in this instance, the deletable voxels are temporarily stored and, of those which are deletable, endpoints are permanently stored, whereas others are deleted.

Next, (6) regarding 6 neighbor voxels of the thus deleted voxels (voxels in which voxels are in contact with each other on the face), voxels having an Euclidean square distance value are included in a group of deletion judgment voxels.

Hereinafter, operations after those given above (4) are repeated until deletable voxels are not found any more. The thus obtained positive number values are all given to be one, thereby obtaining a thinning image.

In the above-described thinning method, a reason for using Euclidean distance is that the rotation of a figure will give a smaller effect on the result of thinning as compared with a case where a deletion judgment is made for border voxels (6-neighbor voxel distance) in three orthogonal axes directions, which is considered to be general and simple. The thinning of a figure which faces in various directions like blood vessels (bronchial tubes) of the lung is considered to provide a more accurate center line, when the Euclidean distance is used.

Figure 5:
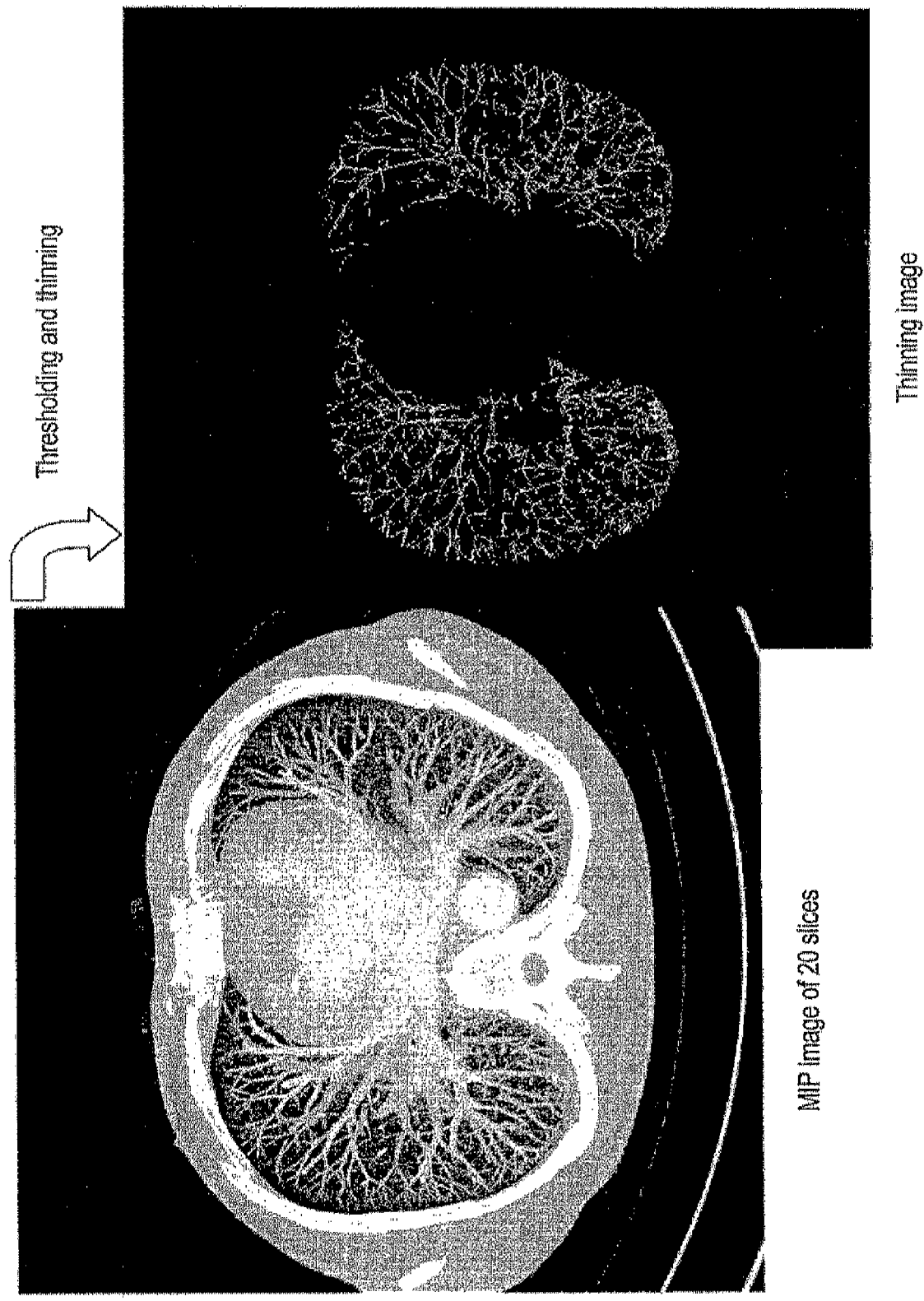
FIG. 5 is a view illustrating procedures for thinning in the first embodiment.

FIG. 5 shows an example of the thinning. Here, a three-dimensional CT image consisting of 512 (pixels)×512 (pixels)×181 (slices) is subjected to thinning. A CT value of a threshold value on thresholding is given as −400. The left side is an image of MIP (maximum intensity projection) of 30 slice portions inside the CT image, and the right side is a thinning image at the same portion. The contrast given on the right side depends on the slice depth.

On extraction of bifurcations by the bifurcation extracting means 24, in the present embodiment, bifurcations of blood vessels (bronchial tubes) inside the lung are used as feature points to be tracked for quantifying movement of the lung. In order to specify the coordinates, a bifurcation 16 of a line figure inside a thinning image 14, which is given as size 1, is taken out and used as a feature point. On extraction of bifurcations, regarding individual voxels inside the thinning image, a voxel in which "the number of one voxel at 26-neighborhood is three" and "a component index is three when a central voxel value is given to be zero at a region of 3×3×3 at the center of the voxel" is used as a bifurcation. Here, the component index means the number of sets of one voxel connected at 26 neighborhood inside a three-dimensional image.

There is a case where the number of extracted bifurcations is extremely large depending on an image. In order to reduce the calculation time in tracking a feature point to be described later, restrict the memory of a computer and remove tracking errors, such a case is eliminated that a plurality of bifurcations exist at a certain neighborhood region.

Figure 6:
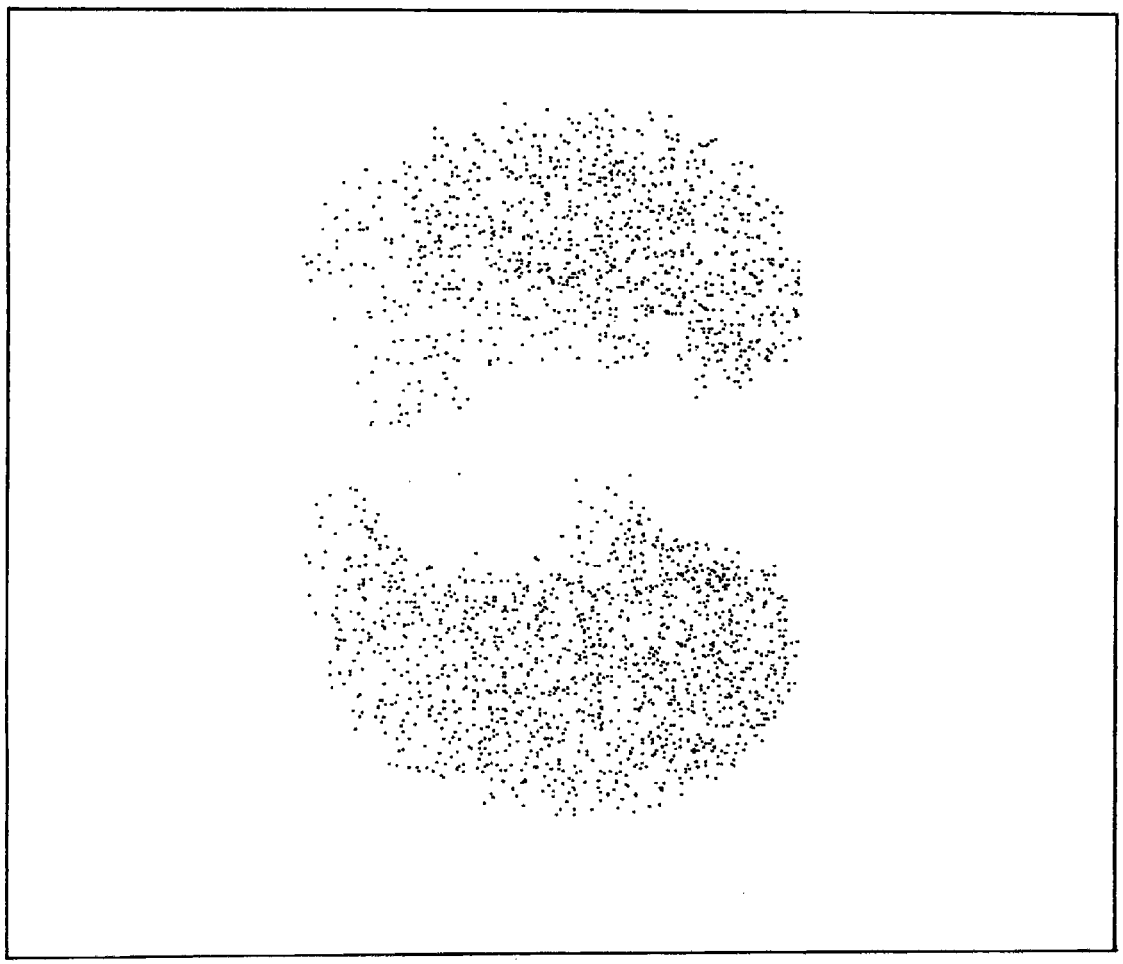
FIG. 6 is a view illustrating the result of extracting bifurcations in the first embodiment.

The above thinning image is subjected to extraction of bifurcations, the result of which is shown in FIG. 6. Here, there is eliminated a case where, of the bifurcations, a plurality of the bifurcations exist in ±2 voxel neighborhoods in each axis direction. About 2400 bifurcations are contained in the image as an entirety, which is sufficient in number in a feature-point tracking process to be conducted later.

In tracking feature points by the feature point tracking means 26, for the purpose of quantifying the deformation of an object between two three-dimensional CT images ($f_0$, $f_1$) obtained at certain minute time intervals, point pattern matching is conducted by referring to the feature points obtained from the respective images as matching point candidates, thereby obtaining matching points of the image $f_1$ with respect to the image $f_0$. The vector obtained by connecting these matching points is given as a displacement vector 18 which represents deformation. Here, the point pattern matching is conducted by a probabilistic relaxation method. This is a method in which the method reported by Barnard et. al., (Stephen T. Barnard and William B. Thompson, "Disparity Analysis of Image," IEEE TRANSACTION OF PATTERN ANALYSIS AND MACHINE INTELLIGENCE, Vol. PAMI-2, No. 4, July 1980, PP333-340) is applied to the three-dimensional images and modified accordingly.

Figure 7:
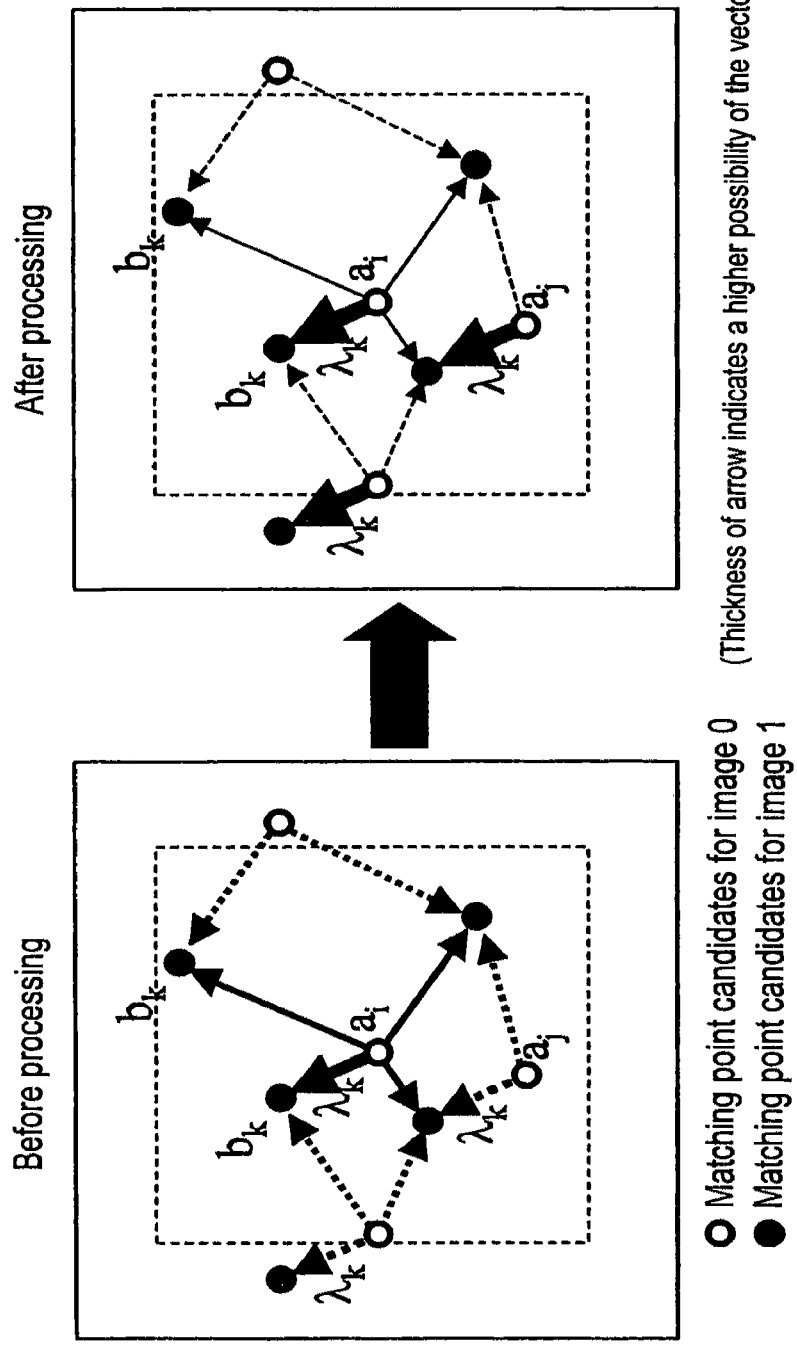
FIG. 7 is a view illustrating procedures for tracking feature points in the first embodiment.

Specifically, as illustrated in FIG. 7, matching point candidates extracted from the images $f_0$, $f_1$ are given respectively as $a_i$ (I=1, 2, . . . , $n_a$), $b_k$ (k=1, 2, . . . , $n_b$). Matching point candidates $b_k$ on the image $f_1$ existing inside a cube having a size of $(2r+1)^3$ voxel at the center of $a_i$ with respect to $a_i$ are given as matching point candidates. The displacement vector 18 is defined as a vector in which $a_i$ is given as a starting point and $b_k$ is given as an ending point. In this stage, since $a_i$ is related as 0 or more of $b_k$, in general, a plurality of candidates for displacement vectors exist with respect to $a_i$. Where the number of candidates for displacement vectors is 0, there is a case where $b_k$ does not exist inside a region to be explored.

A fact that a plurality of candidates for displacement vectors exist with respect to $a_i$ means that an ambiguity exists accordingly. This ambiguity is processed by a relaxation method for narrowing down candidates so that the candidates for displacement vectors obtained for $a_i$ are consistent with those obtained for $a_j$ (j≠i) in the neighborhood of $a_i$. Here, the candidate for displacement vectors is represented by label $\lambda_k$.

$$\lambda_k = (\Delta x_k, \Delta y_k, \Delta z_k) \quad \text{[Formula 1]}$$

Adequacy of each label is defined as label probability. As a result, displacement vectors having a high label probability are judged as a movement to be obtained.

Where $a_i$ has L number of candidates for matching points $b_{kl}$(l=1, 2, . . . , L), $a_i$ has L+1 number of labels. This set of labels is given as $\Lambda_i$.

[Formula 2]

$$\Lambda_i = \{\lambda_{k1}, \lambda_{k2}, \ldots, \lambda_{kL}, \lambda_m\} \quad (1)$$

$$\lambda_{k1} = (x_{k1} - x_i, y_{k1} - y_i, z_{k1} - z_i) \quad (2)$$
$$= (\Delta x_{k1}, \Delta y_{k1}, \Delta z_{k1})$$

Here, $\lambda_m$ represents a label at which no candidate for a matching points is present.

On the assumption of a cube having one side of (2d+1) voxels at the center of $(x_i, y_i, z_i)$ and $(x_{kl}, y_{kl}, z_{kl})$, a similarity between $a_i$ and $b_k$ is defined by the following formula.

[Formula 3]

$$S_1(\lambda_{k1}) = \cfrac{1}{1 + C\left\{\displaystyle\sum_{w=-d}^{d}\sum_{v=-d}^{d}\sum_{u=-d}^{d}\left(\begin{array}{c}f_0(x_i+u, y_i+v, z_i+w) - \\ f_1(x_{k1}+u, y_{k1}+v, z_{k1}+w)\end{array}\right)^2\right\}\Big/(2d+1)^3} \quad (3)$$

In this formula, C stands for a constant number to be established appropriately. Since a value region of $S_i(\lambda_{kl})$ is [0, 1], this value region is used to define an initial label probability $P_i^{(0)}(\lambda_{kl})$ of $a_i$ with respect to $\lambda_{kl}$, which is as follows.

[Formula 4]

$$P_i^{(0)}(\lambda_m) = 1 - \max_l[S_i(\lambda_{k1})] \qquad (4)$$

$$P_i^{(0)}(\lambda_{k1}) = \frac{S_i(\lambda_{k1})}{\sum_{l'} S_i(\lambda_{k1'})}(1 - P_i^{(0)}(\lambda_m))$$

$$(1, 1' = 1, 2, \ldots, L)$$

The label probability $P_i(\lambda_{kl})$ of $a_i$ with respect to label $\lambda_{kl}$ is considered to be consistent with a fact that $a_i$ has $\lambda_{kl}$, if $a_j$ which has a high label probability with respect to $\lambda_{kl}$ exists in the neighborhood of $a_i$, in other words, a feature point of the neighborhood is highly probable in having the same displacement vector. Therefore, in this instance, $a_j$ is renewed so as to have a higher probability. First, the label $\lambda_{kl}$ of $a_i$ is defined for local consistency $Q_i(\lambda_{kl})$ by the following formula.

[Formula 5]

$$Q_i(\lambda_{k1}) = \sum_{j \neq i}\sum_{r} P_j(\lambda_{k1'}) \quad (1 = 1, 2, \ldots, L) \qquad (5)$$

Consideration is given to a case where 1' is a label $\lambda_{kl'}$ of $a_j$ satisfying the following formula, with some positional deviation of T taken into account with respect to the label $\lambda_{kl} = (\Delta x_{kl}, \Delta y_{kl}, \Delta z_{kl})$ of $a_i$.

[Formula 6]

$$\max[|\Delta x_{kl} - \Delta x_{kl'}|, |\Delta y_{kl} - \Delta y_{kl'}|, |\Delta z_{kl} - \Delta z_{kl'}|] \leq T \qquad (6)$$

Here, T is equal to 1. Therefore, the formula (5) represents a sum of label probabilities having a vector, the direction of which is substantially the same, among $a_j$ which is close to $a_i$. Here, a neighborhood point $a_j$ is selected so as to satisfy the following formula.

[Formula 7]

$$\max[|x_i - x_j|, |y_i - y_j|, |z_i - z_j|] \leq \qquad (7)$$

In this formula, R stands for a range of exploring a neighborhood point $a_j$.

The label probability is renewed by using $Q_i(\lambda_{kl})$, which is as follows.

[Formula 8]

$$P_i^{(new)}(\lambda_{k1}) = \frac{P_i^{'(new)}(\lambda_{k1})}{\sum_{l'} P_i^{'(new)}(\lambda_{k1'})} \qquad (8)$$

$$(1, 1' = 1, 2, \ldots, L, m)$$

Here,

[Formula 9]

$$P_i^{'(new)}(\lambda_m) = P_i^{(old)}(\lambda_m) \qquad (9)$$

$$P_i^{'(new)}(\lambda_{kl}) = P_i^{(old)}(\lambda_{kl})(A + BQ_i^{(old)}(\lambda_{kl})) \qquad (10)$$

The formula is expressed as described above, in which A and B are positive constant numbers to be established appropriately.

A process in which the formulae (8), (9) and (10) are used to renew a label probability in parallel (independently) with respect to each of $a_i$ (i=1, 2, . . . , $n_a$) is defined as one repeating process. This process is repeated until there is found no change in label probability (convergence). The repeating process is performed on the order of about 10 times.

As an experimental application of feature-point tracking, the CT image used previously in the thinning process and an image deformed by some calculation (the image is expanded by 5% by referring to one certain point, and a random value having an average value of 0 and a standard deviation of 30 is added to each voxel as a fluctuation of CT value) are used to respectively effect the lung region extraction, thinning and extraction of bifurcations, and the thus obtained results are used to track their feature points. Here, values of individual parameters in point pattern matching by a probabilistic relaxation method are r=15, d=2, C=0.0001, R=15, A=0.3, and B=3.0.

Of label probabilities calculated at each of matching point candidates on an initial CT image, a maximum probability is adopted. As a result, of 2486 points which have a pair of matching point candidates, 1343 points have a displacement vector, whereas remaining points of 1143 do not have a matching point.

Figure 8:
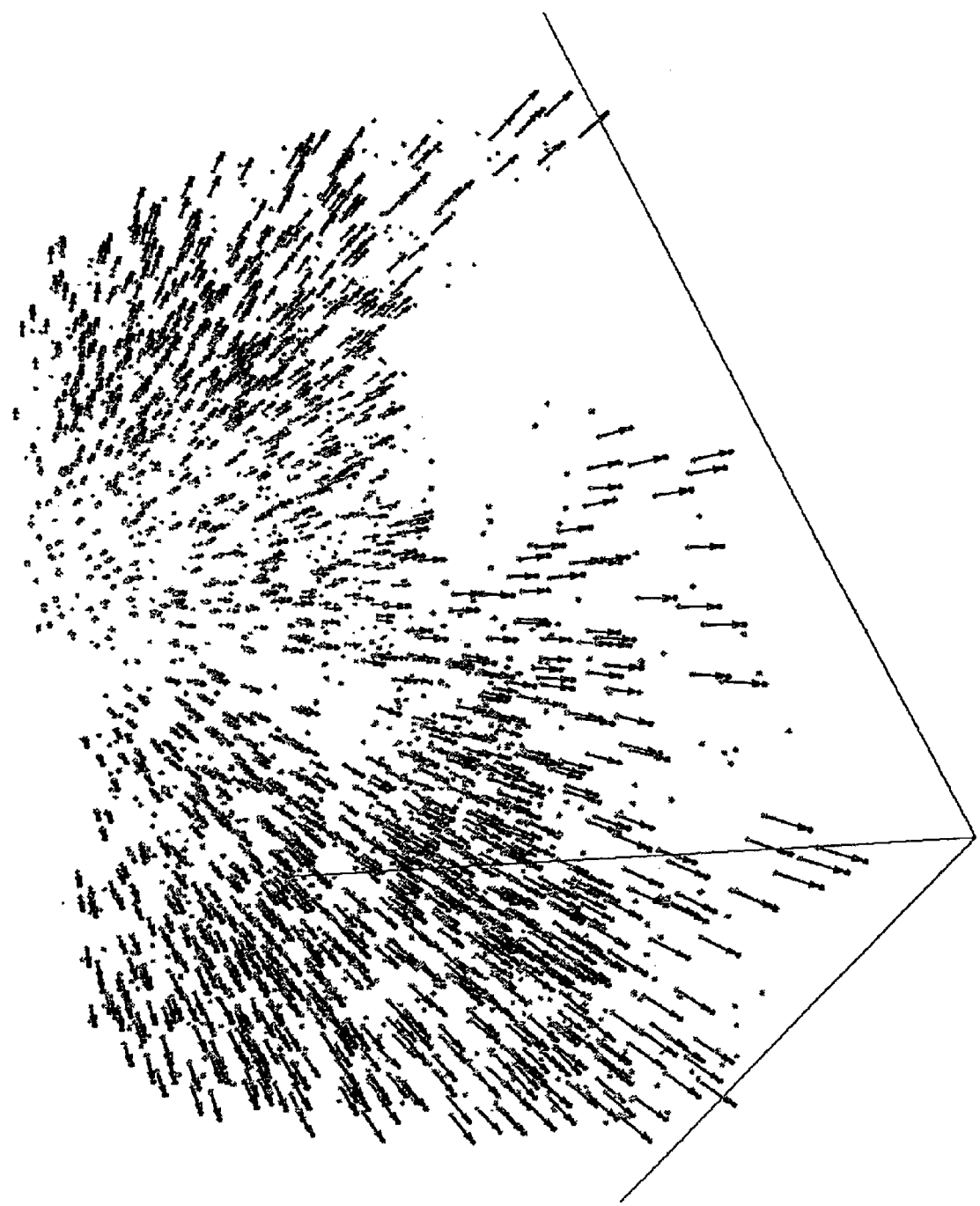
FIG. 8 is a view illustrating displacement vectors calculated in the first embodiment.

FIG. 8 shows the thus obtained displacement vectors. The number of vectors is sufficient for grid interpolation which is performed to quantify the displacement of voxels as a whole.

In order to evaluate the adequacy of displacement vectors obtained as a result of the calculation, a deviation is determined from an ideal value of the vector component concerned. A component of the thus calculated displacement vector is substantially close to an ideal value. However, there is a case where the component is deviated from an ideal value.

The deviation is partially caused by (1) a fluctuation of coordinates on the center line developed on thinning. Where a figure is complicated in configuration, a true center line is placed between voxels or where there is an influence of algorithms on the sequence of voxels or the like used in making a deletion judgment, the fluctuation of about one voxel is found. In other words, about one fluctuation exists in the coordinate of an extracted feature point. An ideal value of the displacement vector component is also an ideal value calculated from the coordinate of a voxel. Therefore, a fluctuation has already been included at a stage where the coordinates of feature points are identified.

The deviation may also be caused by (2) an erroneous recognition in tracking a feature point. There is a possibility that a wrong point may be taken as a matching point in point pattern matching. However, as far as the distribution of deviations is concerned, most of vectors are deviated within about ±1, which may justify a substantially correct calculation. Since the respective voxel sizes in the directions of x, y, z are 0.625, 0.625 and 1 mm for this data, a fluctuation obtained by quantifying movement in this method is concluded to be similar to the above size.

A displacement vector indicates movement relative to a limited number of voxels distributed in a space. However, such displacement is considered to hardly take place that is locally different in displacement vector (a region smaller than a clearance between displacement vectors), and therefore, a displacement quantity relative to all voxels in space can be determined by referring to grid interpolation.

Figure 9:
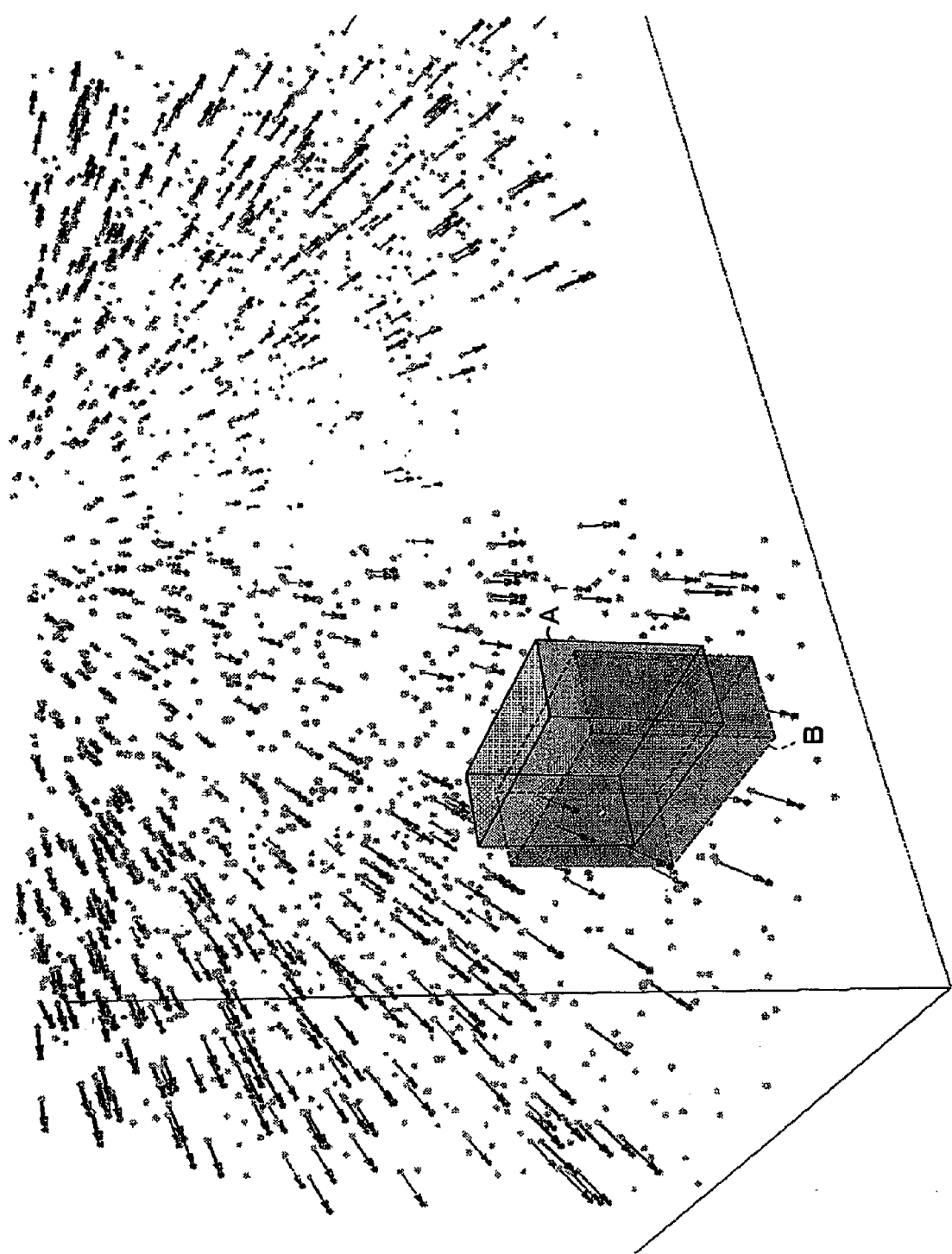
FIG. 9 is a view illustrating an example of calculating the volume after deformation in the first embodiment.

As an application example in which the quantification of movements is used, there is a dose distribution evaluation, with consideration given to movements. In this case, the above method is used to automatically calculate a deformed target volume set by a CT image at a certain time point after deformation. FIG. 9 shows the example. Here, a rectangular-solid region is given for a simple explanation. The rectangular solid shown by the solid line A is a volume which is set accordingly, and the rectangular solid shown by the broken line B is a volume which is calculated by grid interpolation from a displacement vector. Thus, obtained is a rectangular solid which undergoes a substantially correct deformation.

In the above explanation, a target organ is the lung. However, there is no particular restriction on a target organ. A technique such as angiography is used to modify a method for extracting feature points, thereby making it possible to use an organ other than the lung such as the liver as a target in a similar manner.

Next, an explanation will be made by referring to FIG. 10 for a second embodiment of the present invention in which the present invention is used to estimate an organ position so as to irradiate radiation thereto.

Figure 10:
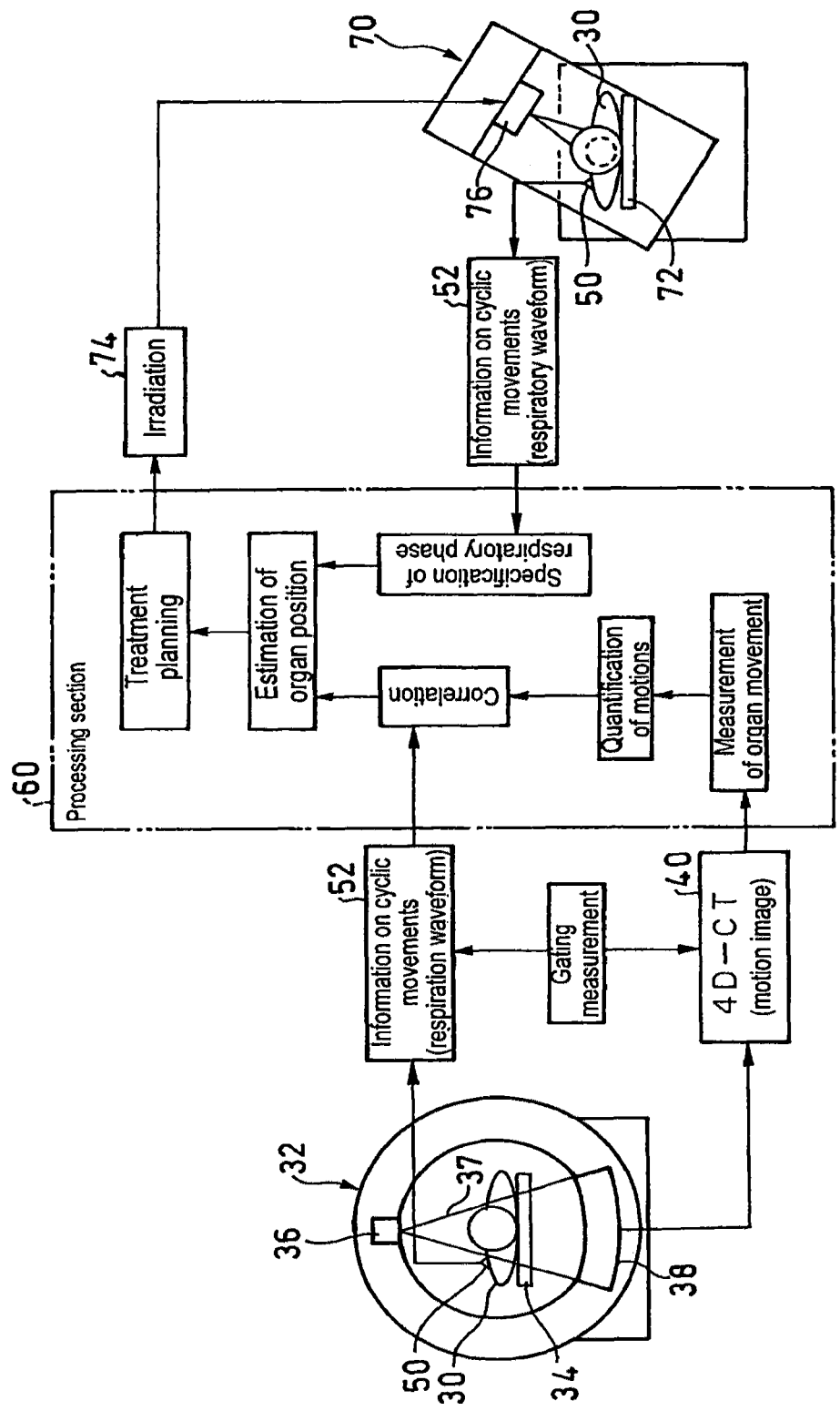
FIG. 10 is a flow chart illustrating procedures in a second embodiment of the present invention.

In the present embodiment as well, as illustrated on the left side in FIG. 10, X-ray 37 is irradiated from an X-ray tube 36 to a patient 30 on a bed 34 inside a CT gantry 32. Then, as with the first embodiment, a four-dimensional CT (4D-CT) 40 is used to process an image obtained by an X-ray detector 38, thereby obtaining an image of organ motion (four-dimensional CT image). At this time, for example, movement-information obtaining means 52 is used to simultaneously calculate a respiratory waveform by referring to a respiration sensor 50 fixed on the body surface of the patient 30, thereby obtaining a temporal correlation between them.

Then, the technology of the first embodiment is used to quantify motions from the four-dimensional CT image at a processing section 60, thereby obtaining motion information at each position. Thus, the above-calculated respiratory waveform is correlated with movement at each position, making it possible to estimate an organ position at an arbitrary respiratory phase.

Next, the thus obtained correlation data is used to make a four-dimensional treatment planning (evaluation of dose given to a tumor and normal tissues and optimization of conditions such as irradiation method), with movement taken into account.

Specifically, as illustrated on the right side in FIG. 10, the movement-information obtaining means 52 is used to calculate a respiratory waveform on a real time basis from the respiration sensor 50 fixed on the body surface of the patient 30 on the bed 72 of a radiation therapy apparatus 70.

Then, a respiratory phase to be irradiated with radiation is specified, the correlation data is used to estimate an organ position on a real time basis, and radiation for medical treatment is irradiated from a radiation irradiating apparatus 76 via an irradiation controller 74 at a necessary timing so as to satisfy the treatment planning.

Next, with reference to FIG. 11 (flowchart showing the procedures) and FIG. 12 (schematic diagram), an explanation will be made for a third embodiment of the present invention in which the present invention is utilized to detect an abnormal organ.

Figure 11:
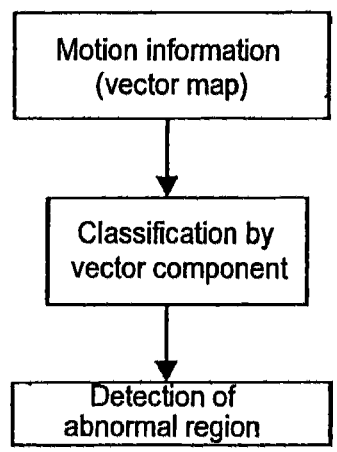
FIG. 11 is a flow chart illustrating procedures in a third embodiment of the present invention.
Figure 12:
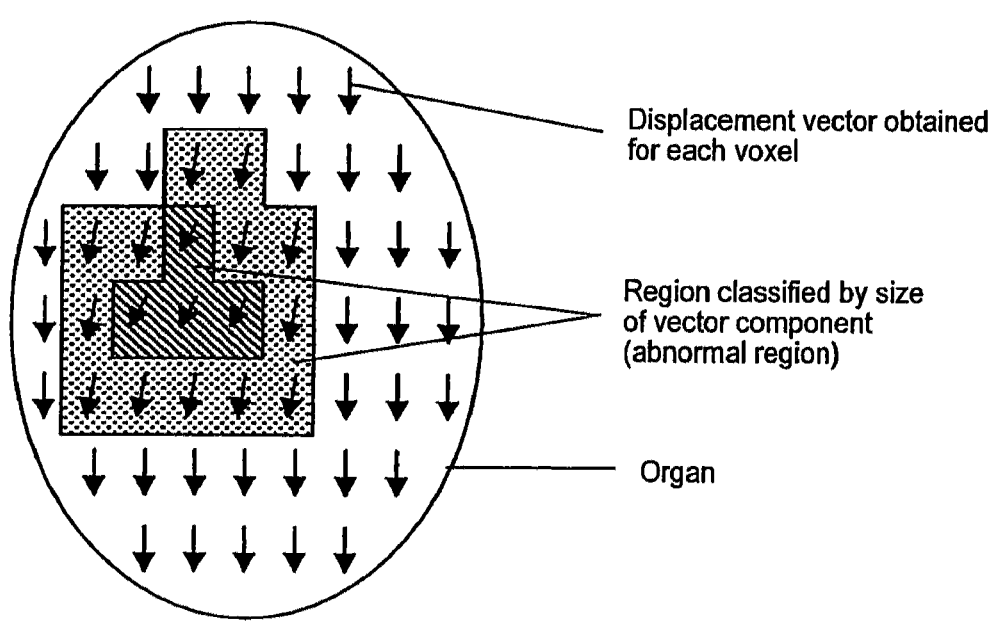
FIG. 12 is a schematic diagram illustrating the third embodiment of the present invention.

In the present embodiment, as the procedures are shown in FIG. 11, displacement vectors for each voxel obtained by the technique of the first embodiment are classified into regions, depending on the vector component concerned, as illustrated in FIG. 12. In other words, as with contour lines obtained depending on the height on each point on a map, regions are classified, depending on the size of components on a vector map, thereby making it possible to extract a region different in displacement. Thereby an abnormal region can be detected.

INDUSTRIAL APPLICABILITY

The present invention can be used to ascertain the matching (registration) of each portion inside an organ with respect to an organ such as a lung which undergoes variation or deformation in association with respiration or the like, the deformation of volume of interest of tumors or the like and position thereof in correlation with a phase of respiratory waveform in radiological diagnosis, treatment planning and medical treatment.

What is claimed is:
1. A method for quantifying organ motion comprising:
using a plurality of CT images of an organ which has undergone a subtle variation or deformation as input data;
extracting, and subjecting to thinning, portions of the plurality of CT images showing blood vessels and trachea distributed inside the organ;
using the thinned images to extract coordinates of bifurcations and connections;
deleting neighboring bifurcations such that a plurality of bifurcations do not exist in a predetermined neighborhood region;
using the extracted coordinates as feature points to track a motion of individual points between the plurality of CT images in a three dimensional space, thereby measuring movement of the organ, the feature points being tracked by point pattern matching in which the plurality of CT images and feature point coordinates are used;
narrowing down point pattern matching candidates using a relaxation method that determines a displacement quantity of each of the feature points; and
changing the thinned images into a line figure that matches with a center line so that the feature points can be estab- lished without changing the thickness and size of the thinned images in topology, the center line having a thickness of one voxel.

2. The method for quantifying organ motion as set forth in claim 1, wherein a plurality of feature points are interpolated for movement, thereby obtaining movement at an arbitrary point.

3. A method for estimating an organ position, wherein dynamic information obtained by a method described in claim 1 is correlated with information on cyclic movements of the organ, thereby estimating the organ position.

4. The method for estimating an organ position as set forth in claim 3, wherein the information on cyclic movements of the organ is a pneumogram.

5. A method for irradiating radiation, wherein radiation is irradiated to a position of the organ estimated by the method described in claim 4.

6. The method for irradiating radiation as set forth in claim 5, wherein at least either the timing or position of irradiation of radiation is made changeable.

7. A method for irradiating radiation, wherein dynamic information obtained by a method described in claim 1 is collected at the same time with a pneumogram, and a correlation between the pneumogram and three-dimensional movements at a target site is ascertained, thereby making it possible to optimize a timing of respiratory gating irradiation on radiation therapy and also estimate a target border position for target tracking irradiation at a high accuracy.

8. An apparatus for quantifying organ motion comprising:
   means for inputting a plurality of CT images of an organ which has undergone a subtle variation or deformation;
   means for extracting and thinning portions of the plurality of CT images showing blood vessels and trachea distributed inside the organ;
   means for extracting coordinates of bifurcations and connections by using the thinned images;
   means for deleting neighboring bifurcations such that a plurality of bifurcations do not exist in a predetermined neighborhood region;
   means for measuring movement of the organ by using these coordinates as feature points to track a motion of individual points between the plurality of CT images in a three dimensional space;
   means for tracking the feature points by conducting point pattern matching in which the plurality of CT images and feature point coordinates are used; and
   means for narrowing down point pattern matching candidates using a relaxation method that determines a displacement quantity of each of the feature points;
   wherein the thinned images are unchanged in topology but are changed into a line figure that matches with a center line so that the feature points can be established, the center line having a thickness of one voxel.

9. The apparatus for quantifying organ motion as set forth in claim 8, which is provided with means for interpolating movement of a plurality of feature points, thereby determining movement at an arbitrary point.

10. An apparatus for estimating an organ position comprising:
    the apparatus described in claim 8; and
    means for estimating an organ position by correlating dynamic information obtained by the apparatus concerned with information on cyclic movements of the organ.

11. The apparatus for estimating an organ position as set forth in claim 10, wherein the information on cyclic movement of the organ is a pneumogram.

12. An apparatus for irradiating radiation comprising:
    means for irradiating radiation at an organ position estimated by the apparatus described in claim 10.

13. The apparatus for irradiating radiation as set forth in claim 12, wherein at least either the timing or position of irradiation of radiation is made changeable.

14. An apparatus for irradiating radiation comprising:
    the apparatus described in claim 8;
    means for collecting dynamic information obtained by the apparatus concerned and a pneumogram at the same time; and
    means for ascertaining a correlation between the pneumogram and three-dimensional movement at a target site; wherein
    it is possible to optimize a timing of respiratory gating irradiation on radiation therapy and estimate a target border position for target tracking irradiation at a high accuracy.

15. An apparatus for detecting an abnormal organ comprising:
    the apparatus described in claim 8; and
    means for ascertaining a locally abnormal deformation of the organ on the basis of dynamic information obtained by the apparatus concerned.

* * * * *